United States Patent [19]

Tenud et al.

[11] 4,443,627

[45] Apr. 17, 1984

[54] PROCESS FOR THE PRODUCTION OF CARNITINE AMIDE

[75] Inventors: Leander Tenud, Visp; René Blum, Binningen, both of, Switzerland

[73] Assignee: Lonza Ltd., Gampel, Switzerland

[21] Appl. No.: 341,009

[22] Filed: Jan. 20, 1982

[30] Foreign Application Priority Data

Jan. 21, 1981 [CH] Switzerland ............................ 363/81

[51] Int. Cl.³ ................. C07C 102/06; C07C 103/183
[52] U.S. Cl. .................................... 564/136; 564/197; 564/198; 564/201
[58] Field of Search ................. 564/136, 197, 198, 201

[56] References Cited

U.S. PATENT DOCUMENTS

| | | | |
|---|---|---|---|
| 2,087,565 | 7/1937 | Balle et al. ...................... | 564/198 X |
| 3,072,722 | 1/1963 | Aspergren et al. ............. | 564/198 X |
| 3,096,244 | 7/1963 | Ehrhart et al. ................. | 564/201 X |
| 3,155,658 | 11/1964 | Rogier ............................ | 564/198 X |
| 3,462,485 | 8/1969 | Binon et al. ..................... | 564/198 X |
| 4,254,053 | 3/1981 | de Witt et al. .................. | 564/198 X |

FOREIGN PATENT DOCUMENTS 242906  1/1960  Australia .............................. 564/198

*Primary Examiner*—Thomas A. Waltz
*Attorney, Agent, or Firm*—Fisher, Christen & Sabol

[57] ABSTRACT

Process for the production of carnitine amide in the form of a chloride. The carnitine ethyl ester is obtained by reaction of 4-chloroacetoacetic acid ethyl ester with trimethyl amine and the subsequent hydrogenation is carried out with the help of a Pt/C catalyst. Such carnitine ethyl ester, without isolating it, is reacted with ammonia in an autoclave at −30° to +10° C. Everything is heated to 40° to 80° C. The mixture is stirred at such temperature at an ammoniac pressure of 8 to 24 atu. The product is filtered after cooling it to ambient temperature and counterbalancing the excess pressure. The product is then washed with alcohol and subsequently dried at 30° to 50° C. and at a pressure of 15 to 25 torr.

8 Claims, No Drawings

PROCESS FOR THE PRODUCTION OF CARNITINE AMIDE

BACKGROUND OF THIS INVENTION

1. Field of this Invention

This invention relates to a process for the production of carnitine amide in the form of its chloride.

2. Prior Art

It has been known to produce carnitine amide chloride from carnitine nitrile.

In the case of one method according to Belgian Pat. No. 659,194, the carnitine nitrile produced from epichlorohydrin is reacted by means of hydrolysis with concentrated hydrochloric acid at 15° to 55° C. over a period of 46 to 48 hours. In that case, carnitine hydrochloride and ammonium chloride develop which negatively influence the quality of the desired product.

Another procedure which is described in Japanese Patent Publication No. 23 (1963) involves the treatment of carnitine nitrile chloride with an excess of hydrogen peroxide in a basic environment. Despite a good yield, that process has the very large disadvantage of being uneconomical. Hydrogen peroxide is relatively expensive and one must operate that process with a great excess of it.

BROAD DESCRIPTION OF THIS INVENTION

An object of this invention is to provide a process which eliminates the disadvantages of the above-described prior art methods. Other objects and advantages of this invention are set out herein or are obvious herefrom to one ordinarily skilled in the art.

The objects and advantages of this invention are achieved by the process of this invention.

This invention involves a process for the production of carnitine amide in the form of a chloride. The carnitine ethyl ester is obtained by the reaction of 4-chloroacetoacetic acid ethyl ester with trimethyl amine and the subsequent hydrogenation is carried out with the help of a Pt/C catalyst. The carnitine ethyl ester therefrom is reacted with ammonia without isolating it in an autoclave at −30° to +10° C. Everything is then heated to 40° to 80° C. The mixture is stirred at such temperature at an ammoniac pressure of 8 to 24 atu. The product thusly obtained is filtered after cooling it to ambient temperature and counterbalancing the excess pressure. The filtered product is washed with ethyl alcohol and subsequently dried at 30° to 50° C. and at a pressure of 15 to 25 torr.

Preferably the aminolysis is carried out at a temperature of 50° to 70° C. Preferably the stirring time in the autoclave is 4 to 6 hours. Also preferably the ammoniac excess pressure in the autoclave is 9 to 15 atu. Preferably the concluding drying process is carried out at 35° to 45° C. in a vacuum of 10 to 20 torr.

By means of the process of this invention carnitine amide chloride can be produced practically in one operation with good yields from 4-chloroacetoacetic acid ethyl ester via the carnitine ester obtained only in the case of such process, without isolating said carnitine ester. The advantages of this invention, as compared to the prior art, include:

A direct process without isolation of intermediate products.

The course of the process permits a removal of the ammonium chloride obtained which is disturbing in the end product.

The end product is free of carnitine hydrochloride.

The space/time yield is very large.

The process of this invention proceeds according to the following scheme:

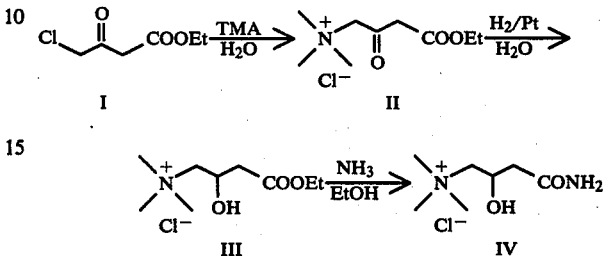

Notes:
I = 4-chloroacetoacetic acid ethyl ester
II = dehydrocarnitine ester
III = carnitine ester
IV = carnitine amide chloride
TMA = trimethylamine The process of this invention is characterized by the fact that carnitine ester obtained as an intermediate product does not need to be isolated.

By way of summary, this invention is a process for the production of carnitine amide in the form of the chloride from 4-chloroacetoacetic acid ethyl ester, without having to isolate the carnitine ester obtained as an intermediate product.

DETAILED DESCRIPTION OF THIS INVENTION

As used herein, all parts, percentages, ratios and proportions are on a weight basis unless otherwise stated herein or otherwise obvious herefrom to one ordinarily skilled in the art.

Effectively, the straight-line and direct process of this invention is carried out as follows: The quantity of trimethylamine (TMA) provided is put up and is slowly dosed in at about 10° C. to the 4-chloroacetoacetic acid ethyl ester. The excess TMA is precipitated out and recaptured from the yellowish reaction mixture which had been brought to a pH of 7 to 8 by concentrating it. The whole mixture is slightly acidified with hydrochloric acid, is filtered and is catalytically hydrogenated in an autoclave under pressure. As the catalyst, platinum on activated charcoal is preferred. The residue (freed of catalyst, concentrated and dried at 30° to 40° C. at 0.1 to 0.2 torr) is dissolved in ethyl alcohol. The ethanol solution is saturated for about 1 hour at ambient temperature with gaseous ammonia and the ammonium chloride obtained is filtered out. Subsequently, ammonia is added to the filtrate in an autoclave at −30° C. and the whole mixture is stirred for 3 to 20 hours (preferably 4 to 6 hours) at 40° to 80° C. (preferably at 50° to 70° C.) at a pressure of 8 to 24 atu. (preferably at 9 to 15 atu.). After completion of the reaction and after cooling the reaction mixture to ambient temperature, the precipitated carnitine amide chloride is filtered out and washed with ethyl alcohol. The carnitine amide chloride is dried in the drying cabinet at 30° to 50° C. (effectively at 35° to 45° C.) and 15 to 25 torr (preferably at 10 to 20 torr) to a constant weight. The yields which are thusly achieved, amount to about 80 percent of 100 percent carnitine amide, calculated on 100 percent of the 4-chloroacetoacetic acid ethyl ester used.

EXAMPLE 1

In a 2.5 liter double casing vessel, equipped with a discharge cock, a mechanical stirrer and thermometer, 1062.7 g of trimethylamine (44.5 percent in water=472.9 g, 100 percent=8 mole) was put up and cooled to 10° C. By means of a dosing pump and a hose submerged in the TMA solution, 272.8 g of 4-chloroacetoacetic acid ethyl ester (96.0 percent=261.9 g, 100 percent=1.59 mole) was added by doses during 3 hours at 10° to 12° C. and the yellowish reaction mixture was concentrated at 40° C. and 25 torr in such manner until the pH value reached 7.6. The excess TMA was subsequently condensed out by means of three cooling traps and was recaptured. After a slight lowering of the pH value with 65 ml of 36% hydrochloric acid to 6 and after the filtering out of the yellowish precipitate obtained (2,5-diethoxycarbonyl-1,4-cyclohexadiene), the reaction solution was hydrogenated in a 2-liter autoclave equipped with a stirring mechanism for 7 hours at 10° C. and 11 atu of pressure with the help of 8.8 g of platinum/activated charcoal catalyst.

After the catalyst had been filtered off, following the completed hydrogenation, the filtrate was completely condensed in a Rotavapor at 50° C. and 30 torr. The filtrate was subsequently dried in high vacuum (5 hours at 30° to 40° C. and at 0.1 to 0.2 torr) and the residue was dissolved in 295 g of absolute ethyl alcohol. A part of this solution, in this case a quantity containing 154.9 g of crude carnitine ester (corresponding to 0.4 mole of 4-chloroacetoacetic acid ethyl ester), was saturated for 1 hour at ambient temperature with gaseous ammonia. 7.7 g of ammonium chloride was precipitated and filtered off. The filtrate was subsequently placed in a 1-liter autoclave equipped with a stirring mechanism, was cooled to −30° C. and was reacted with 75 g of ammonia. After closing the pressure reactor, the temperature was raised to 60° C. and the reaction mixture was stirred for 5 hours at 250 rpm. When reaching the above mentioned 60° C., enough ammonia was discharged so that the operating pressure was 10 atu.

At the end of the reaction, the entire system was cooled to ambient temperature and the autoclave was released of tension (pressure).

The deposited carnitine amide chloride was filtered off, washed twice with 100 g of ethyl alcohol at 20° C. and dried in a drying cabinet at 40° C. and 20 torr to a constant weight.

The yield amounted to 63.0 g of 99.1 percent carnitine amide chloride, which corresponded to 62.4 g of the 100 percent substance, and this is equated to 79.3 percent of theoretical, based on 100 percent 4-chloroacetoacetic acid ethyl ester.

EXAMPLES 2 TO 8

Examples were carried out according to the method of Example 1. The variations therefrom are apparent from the following table:

TABLE

| Example No. | Crude Ester H$_2$O Weight Percent | Ester Concentrate, Weight Percent | Pressure, atu. | Ammonia, Mole Equivalent | T, °C. | Time, h | Yield,[1] % |
|---|---|---|---|---|---|---|---|
| 2 | 3.1 | 44 | 8 | 11 | 45 | 20 | 82.5 |
| 3 | 2.0 | 47 | 10 | 10 | 60 | 20 | 85.3 |
| 4 | 1.7 | 35 | 24 | 30 | 80 | 3 | 79.3 |
| 5 | 2.5 | 35 | 10 | 20 | 40 | 7 | 79.7 |
| 6 | 3.2 | 45 | 10 | 7 | 80 | 3 | 78.4 |
| 7 | 6.3 | 40 | 10 | 10 | 60 | 5 | 79.6 |
| 8 | 2.9 | 41 | 10 | 22 | 40 | 14 | 82.2 |

Note:
[1]Yield related to 100 percent 4-chloroacetoacetic acid ethyl ester content: 99 percent

What is claimed is:

1. Process for the production of carnitine amide in the form of a chloride, which comprises (i) reacting 4-chloroacetoacetic acid ethyl ester with trimethyl amine, (ii) hydrogenating the reaction product of step (i) with a Pt/C catalyst, carnitine ethyl ester resulting, (iii) reacting the carnitine ethyl ester, without isolating it, with ammonia in an autoclave at −30° to +10° C., (iv) heating the contents of the autoclave to 40° to 80° C., (v) stirring the mixture at such temperature at an ammoniac pressure of 8 to 24 atu, (vi) cooling the carnitine amide chloride to ambient temperature and counterbalancing the excess pressure, (vii) filtering the carnitine amide chloride, (viii) washing the carnitine amide chloride with ethyl alcohol, and (ix) drying the carnitine amide chloride at 30° to 50° C. and at a pressure of 15 to 25 torr.

2. Process as claimed in claim 1 wherein the aminolysis is carried out at a temperature of 50° to 70° C.

3. Process as claimed in claim 1 wherein the stirring time in the autoclave is 4 to 6 hours.

4. Process as claimed in claim 3 wherein the ammoniac excess pressure in the autoclave is 9 to 15 atu.

5. Process as claimed in claim 4 wherein the concluding drying process is carried out at 35° to 45° C. and in a vacuum of 10 to 20 torr.

6. Process as claimed in claim 1 wherein the ammoniac excess pressure in the autoclave is 9 to 15 atu.

7. Process as claimed in claim 1 wherein the concluding drying process is carried out at 35° to 45° C. and in a vacuum of 10 to 20 torr.

8. Process as claimed in claim 1 wherein the aminolysis is carried out at a temperature of 50° to 70° C., the stirring time in the autoclave is 4 to 6 hours, the ammoniac excess pressure in the autoclave is 9 to 15 atu., and the concluding drying process is carried out at 35° to 45° C. and in a vacuum of 10 to 20 torr.

* * * * *